(12) United States Patent
Chou et al.

(10) Patent No.: US 9,675,515 B2
(45) Date of Patent: Jun. 13, 2017

(54) MOBILITY AID WITH REHABILITATIVE AND GUIDING FUNCTIONS AND REHABILITATION AND GUIDING METHOD THEREOF

(71) Applicant: CHIMEI MEDICAL CENTER, Tainan (TW)

(72) Inventors: Willy Chou, Tainan (TW); Jhi-Joung Wang, Tainan (TW); Jiun-Hung Lin, Tainan (TW)

(73) Assignee: Chimei Medical Center, Tainan (TW)

( * ) Notice: Subject to any disclaimer, the term of this patent is extended or adjusted under 35 U.S.C. 154(b) by 0 days.

(21) Appl. No.: 14/696,608

(22) Filed: Apr. 27, 2015

(65) Prior Publication Data

US 2016/0309861 A1   Oct. 27, 2016

(51) Int. Cl.

| | |
|---|---|
| *A61H 3/00* | (2006.01) |
| *A45B 9/00* | (2006.01) |
| *A61B 5/11* | (2006.01) |
| *A45B 3/08* | (2006.01) |
| *G01C 23/00* | (2006.01) |
| *G08B 7/06* | (2006.01) |
| *A45B 3/04* | (2006.01) |
| *G01S 15/88* | (2006.01) |
| *A61B 5/00* | (2006.01) |
| *G01S 15/02* | (2006.01) |

(52) U.S. Cl.
CPC .................. *A61H 3/00* (2013.01); *A45B 3/04* (2013.01); *A45B 3/08* (2013.01); *A45B 9/00* (2013.01); *A61B 5/112* (2013.01); *A61B 5/1114* (2013.01); *A61B 5/6895* (2013.01); *A61B 5/746* (2013.01); *G01C 23/00* (2013.01); *G01S 15/88* (2013.01); *G08B 7/066* (2013.01); *A45B 2009/002* (2013.01); *A61B 2503/08* (2013.01); *A61B 2505/09* (2013.01); *A61B 2562/0219* (2013.01); *G01S 15/02* (2013.01)

(58) Field of Classification Search
CPC ........ A61H 3/04; A61H 3/061; A61H 1/0262; A61H 2201/5071; A61H 2201/5058; A61H 3/00; A45B 9/00
USPC ......................................................... 340/4.1
See application file for complete search history.

(56) References Cited

U.S. PATENT DOCUMENTS 5,575,294 A * 11/1996 Perry ........................ A45B 3/00
                                                          362/102
7,963,294 B1 * 6/2011 Trout ........................ A61H 3/00
                                                           135/66

(Continued)

*Primary Examiner* — Thomas Alunkal
(74) *Attorney, Agent, or Firm* — Rosenberg, Klein & Lee

(57) ABSTRACT

A mobility aid with rehabilitative and guiding functions includes a main body, a processing unit, a guiding module, a detection module, an inertia sensor, a recording module, and an electricity module. A rehabilitation and guiding method includes the steps of: A) constantly projecting a visible light beam to a next-step position of the mobility aid; B) moving the mobility aid to its next-step position under the guidance of the visible light beam; C) constantly emitting an ultrasonic wave to a next-step position of at least one of the user's feet to define a detection area; D) detecting whether the foot is moved into the detection area; E) recording the moving process of any of the steps A through D and notifying a remote device of the moving process; and F) detecting any of the steps A through D and, if an abnormal condition occurs, sending out a warning message.

10 Claims, 10 Drawing Sheets

(56) References Cited

U.S. PATENT DOCUMENTS

| | | | |
|---|---|---|---|
| 9,125,790 B2* | 9/2015 | Van Gerpen | A61H 3/04 |
| 2006/0163829 A1* | 7/2006 | Livengood | A61G 12/001 |
| | | | 280/87.021 |
| 2006/0292533 A1* | 12/2006 | Selod | A63B 71/0686 |
| | | | 434/247 |
| 2010/0100013 A1* | 4/2010 | Hu | A61H 3/00 |
| | | | 600/595 |
| 2010/0154851 A1* | 6/2010 | Gorey | A45B 3/04 |
| | | | 135/66 |
| 2013/0014790 A1* | 1/2013 | Van Gerpen | A61H 3/04 |
| | | | 135/66 |
| 2013/0103226 A1* | 4/2013 | Fu | A61H 3/04 |
| | | | 701/1 |
| 2015/0066242 A1* | 3/2015 | Tanaka | A61H 3/04 |
| | | | 701/1 |
| 2015/0066328 A1* | 3/2015 | Nakada | A61H 3/04 |
| | | | 701/93 |
| 2016/0045386 A1* | 2/2016 | Sandler | A61B 5/7415 |
| | | | 623/24 |

* cited by examiner

MOBILITY AID WITH REHABILITATIVE AND GUIDING FUNCTIONS AND REHABILITATION AND GUIDING METHOD THEREOF

BACKGROUND OF THE INVENTION

1. Technical Field

The present invention relates to a mobility aid with rehabilitative and guiding functions and a rehabilitation and guiding method thereof. More particularly, the present invention relates to a mobility aid for guiding a physically challenged person during a rehabilitation exercise and to a method of use of the mobility aid.

2. Description of Related Art

Nowadays, one who has an injured leg or other mobility problems or needs rehabilitation would generally use a quadruped walking stick, walker, or other mobility aid for support and assistance while walking. The structure of a common mobility aid is described in Taiwan Patent Application Publication No. 201002304, entitled "CANE STRUCTURE" and published on Jan. 16, 2010, which discloses a cane structure comprising: a cane body including at least one holding portion; a sensor provided at the holding portion and configured for sensing, comparing, and determining the difference between a user's current cardiopulmonary data and the data in an alarm range as previously input by the user; an alarm device connected to the sensor and configured for notifying people nearby with a buzzing sound and sending a signal to a remote receiver and a database; and an electricity unit connected to the sensor and the alarm device and configured for driving the sensor and the alarm device into operation. The alarm device further includes a data transmission interface for receiving signals sent back from the remote receiver and the database. The cane body further includes an accommodating space or/and can be attached with a portable box in order for the user to carry medicine. Thus, the cane features real-time medical assistance, medicine storage, medical information transmission and receiving, and satellite positioning.

In addition, Taiwan Patent No. 1396515, entitled "CANE CAPABLE OF SENSING PRESSURE TO CONTROL ROD LENGTH AND ROD LENGTH CONTROL METHOD THEREOF" and issued on May 21, 2013, discloses a cane comprising a holding portion, a lead screw, a rod, a control module, and a supporting portion. The holding portion and the supporting portion are equipped with a plurality of pressure sensing units for sensing the pressure with which the holding portion is held and the pressure with which the supporting portion contacts with the ground and for generating a plurality of holding pressure values and feedback pressure values. The rod is connected to the holding portion. A motor is provided at the supporting portion. The lead screw has one end engaged with the motor and the other end pivotally connected with the rod. Based on the holding pressure values and the feedback pressure values, the control module determines whether the holding portion is held. When the cane is tilted, the control module instructs the motor to rotate, thereby driving the lead screw into pivotal rotation; as a result, the length of the cane is increased or decreased as the lead screw and the rod are translated in opposite directions.

The mobility aids in the afore-cited patent application and patent leave something to be desired in use because they only have such functions as alarming, satellite positioning, and automatic length adjustment but do not provide guiding assistance in rehabilitation exercises.

SUMMARY OF THE INVENTION

In view of the aforesaid shortcoming of the existing mobility aids and their rehabilitation methods, the present invention provides a mobility aid having both rehabilitative and guiding functions, wherein the mobility aid includes a main body, a processing unit, a guiding module, a detection module, an inertia sensor, and a recording module. The main body has a control box, a handle, and a quadruped base. The processing unit is provided in the control box. The guiding module is provided in the control box and is signal-connected to the processing unit and a transmitter. The transmitter is provided in the control box and is controlled by a first power element configured for driving the transmitter to rotate as needed and to constantly project a visible light beam to the ground at a position in front of the main body. The detection module is provided in the control box and is signal-connected to the processing unit and a detector. The detector is provided in the control box and is controlled by a second power element configured for driving the detector to rotate as needed and to constantly emit an ultrasonic wave to the ground at a position abreast of the main body. The inertia sensor is provided in the control box and is signal-connected to the processing unit. The inertia sensor includes an accelerometer, an angular velocity sensor, and a weight sensor, wherein the weight sensor is provided in the handle. The recording module is provided in the control box and is signal-connected to the processing unit. The recording module is provided with a wireless communication element and is configured for recording the data processed and computed by the processing unit and for transmitting the data through the wireless communication element to a remote device. The recording module is also provided with an alarm element for sending out a warning message.

Preferably, the mobility aid further includes an electricity module provided in the control box. The electricity module is separately electrically connected to the processing unit, the guiding module, the detection module, the inertia sensor, and the recording module in order to provide electricity to the aforesaid components separately.

Preferably, the first power element and the second power element are a servomotor or stepper motor and are provided in the control box, and the alarm element includes a loudspeaker and a warning light.

Preferably, the mobility aid is a quadruped walking stick or a walker.

The present invention also provides a rehabilitation and guiding method of a mobility aid, wherein the method includes the steps of: A) constantly projecting a visible light beam, by the mobility aid, to a next-step position of the mobility aid; B) moving the mobility aid to the next-step position of the mobility aid under the guidance of the visible light beam; C) constantly emitting an ultrasonic wave, by the mobility aid, to a next-step position of at least one of the user's feet to define a detection area; D) detecting whether the at least one of the user's feet is moved into the detection area; and E) recording the moving process of any of the steps A, B, C, and D and notifying a remote device of the moving process.

Preferably, the rehabilitation and guiding method further includes the step F of detecting the moving process of any of the steps A, B, C, and D and, if an abnormal condition occurs, sending out a warning message and notifying the remote device.

Preferably, the abnormal condition in the step F includes at least one of the following: a quadruped base of the mobility aid is not placed at the next-step position of the mobility aid as indicated by the visible light beam, the mobility aid topples or is tilted, the mobility aid is moved at an abnormal speed, and a handle of the mobility aid is not held with a proper force.

Preferably, the step E includes: detecting, by an inertia sensor, information of the mobility aid while the mobility aid is being moved, wherein the information includes acceleration, tilt, impact received, vibration, rotation, and multi-degree of freedom (DOF) motion; recording the information by a recording module; and transmitting the information through a wireless communication element to the remote device, wherein the remote device is selected from the group consisting of a computer, a server, and a smartphone.

Preferably, the step A includes: setting the stride length of a rehabilitative walk according to a rehabilitation condition; inputting the stride length and the required number of steps into a processing unit; and rotating a transmitter to a proper angle according to a computation result such that the transmitter constantly projects the visible light beam to the next-step position of the mobility aid, wherein the next-step position of the mobility aid is on the ground and in front of the mobility aid.

Preferably, the step C includes: setting the stride length of a rehabilitative walk according to a rehabilitation condition; inputting the stride length and the required number of steps into a processing unit; rotating a detector to a proper angle according to a computation result such that the detector constantly emits the ultrasonic wave to the next-step position of the at least one of the user's feet to define the detection area, wherein the next-step position of the at least one of the user's feet is on the ground and in front of the at least one of the user's feet; and detecting the detection area.

The detection area of the ultrasonic wave is abreast of the main body of the mobility aid.

One of the advantageous features of the present invention is that a person with mobility problems can carry out rehabilitation on his or her own. The visible light beam (e.g., laser beam) will indicate the next-step position of the mobility aid, thereby guiding the user to move the mobility aid to the indicated position during a rehabilitation exercise.

Another one of the advantageous features of the present invention is that whether the user's feet land in the ultrasonic wave detection area is detected, thereby determining whether the intended stride length of a rehabilitative walk is achieved.

Still another one of the advantageous features of the present invention is that should any abnormal condition occur to the user, a timely feedback will be produced to prompt corrective actions. Or when there is danger, a message will be sent out for help.

DETAILED DESCRIPTION OF THE INVENTION

Figure 1:
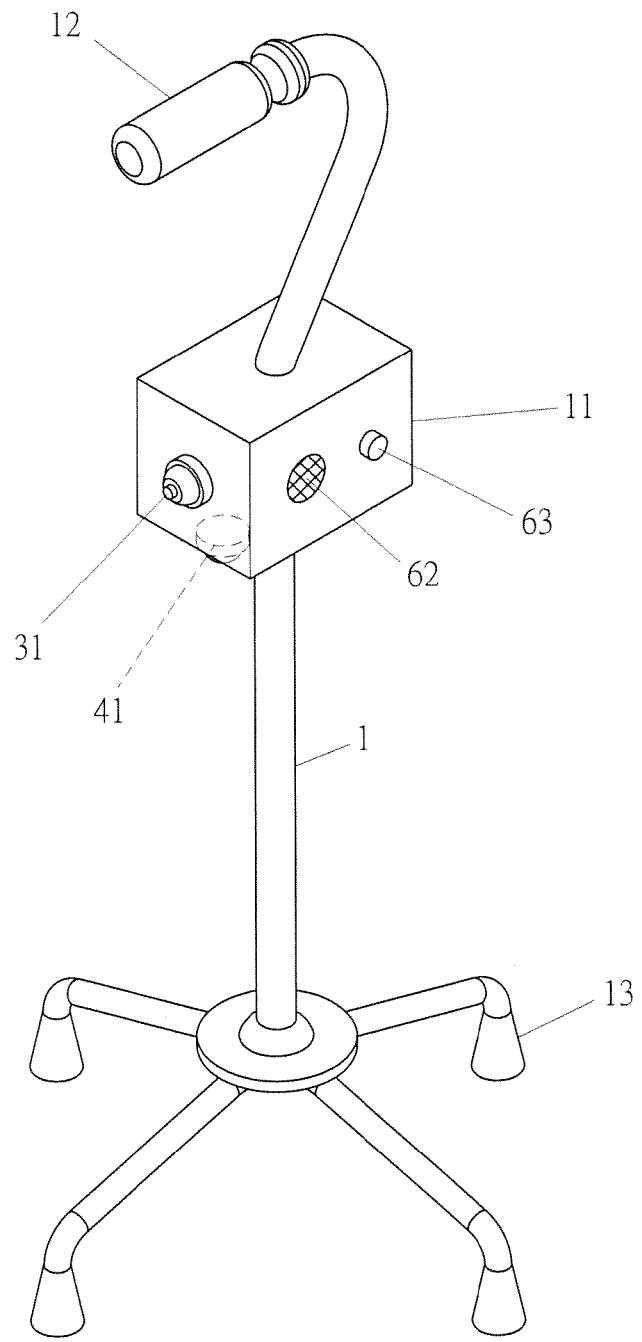
FIG. 1 is a perspective view of the quadruped walking stick in a first embodiment of the present invention.
Figure 2:
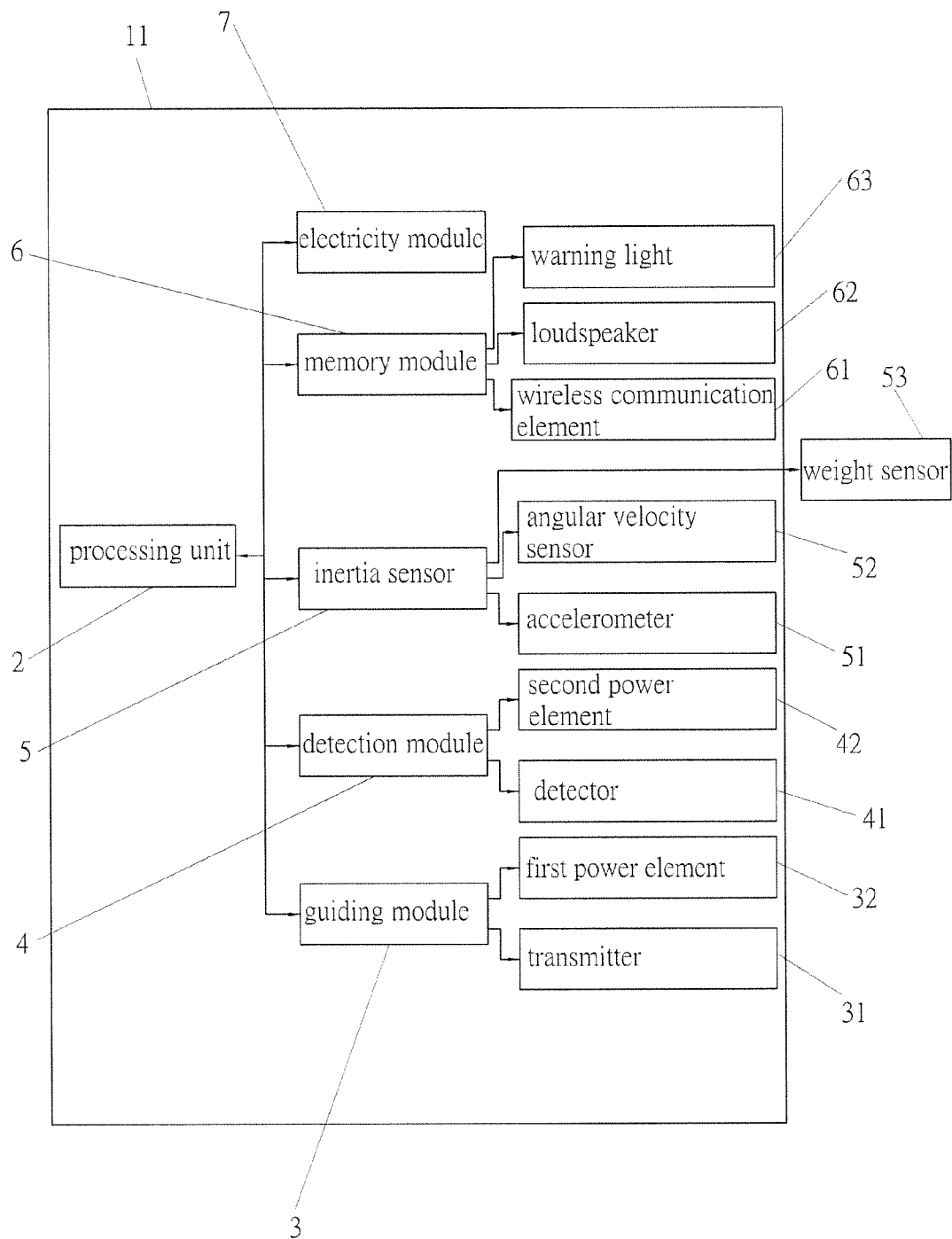
FIG. 2 is a block diagram of the quadruped walking stick in the first embodiment of the present invention.

In one embodiment, the mobility aid having rehabilitative and guiding functions of the present invention is implemented as a quadruped walking stick. Referring to FIG. 1 and FIG. 2, the quadruped walking stick in this embodiment of the present invention includes a main body 1, a processing unit 2, a guiding module 3, a detection module 4, an inertia sensor 5, a recording module 6, and an electricity module 7.

Figure 3:
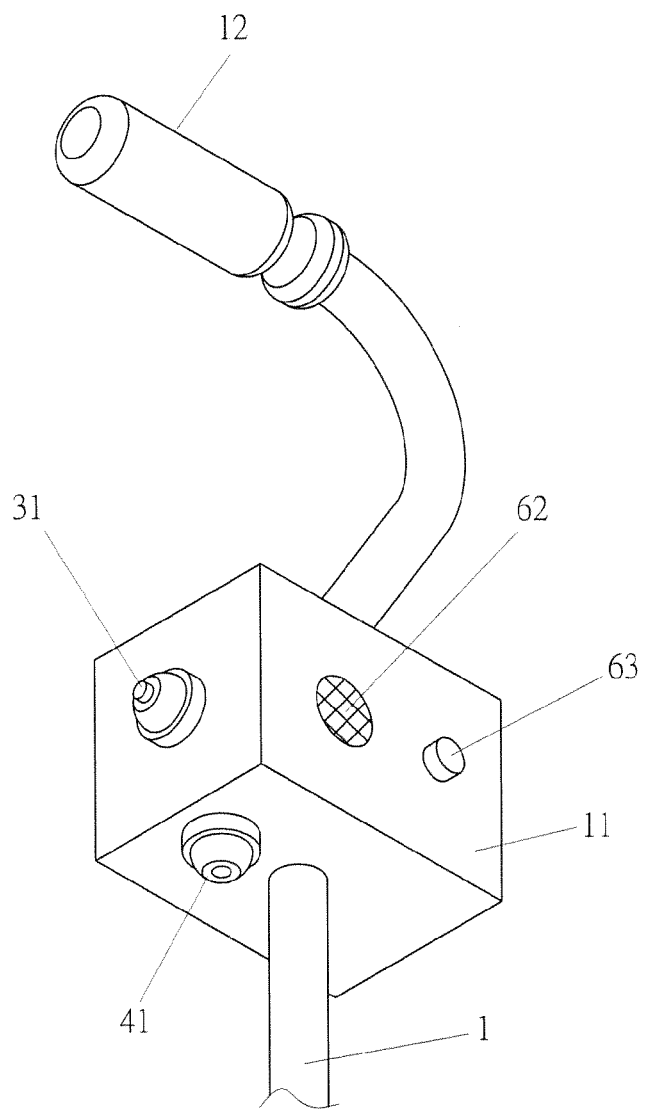
FIG. 3 is a perspective view of the control box of the quadruped walking stick in the first embodiment of the present invention.

The main body 1 is provided with a control box 11 (see FIG. 3) at a proper position. In addition, the main body 1 is provided with a handle 12 at the top end and a quadruped base 13 at the bottom end.

The processing unit 2 is provided in the control box 11 of the main body 1.

The guiding module 3 is provided in the control box 11 of the main body 1. The guiding module 3 is signal-connected to and is controlled by the processing unit 2. The guiding module 3 is also signal-connected to a transmitter 31. The transmitter 31 is provided at an exterior side of the control box 11 and is controlled by a first power element 32. The first power element 32 can be a servomotor or stepper motor and is provided in the control box 11. The first power element 32 is configured for driving the transmitter 31 to rotate through 360° as needed and to constantly project a visible light beam (e.g., laser beam) to the ground at a position in front of the main body 1.

The detection module 4 is provided in the control box 11 of the main body 1. The detection module 4 is signal-connected to and is controlled by the processing unit 2. The detection module 4 is also signal-connected to a detector 41. The detector 41 is provided at an exterior side of the control box 11 and is controlled by a second power element 42. The second power element 42 can be a servomotor or stepper motor and is provided in the control box 11. The second power element 42 is configured for driving the detector 41 to rotate through 360° as needed and to constantly emit an ultrasonic wave to the ground at a position lateral to the main body 1 such that an ultrasonic wave detection area is defined abreast of the main body 1.

The inertia sensor 5 is provided in the control box 11 of the main body 1. The inertia sensor 5 is signal-connected to and is controlled by the processing unit 2. The inertia sensor 5 includes an accelerometer 51, an angular velocity sensor 52 (e.g., a gyroscope), and a weight sensor 53. The inertia sensor 5 may alternatively include a 1 to 3-axis inertia measurement unit (IMU) and an attitude and heading reference system (AHRS) with magnetometers. The inertia sensor 5 serves to detect and measure the acceleration, tilt, impact received, vibration, rotation, and multi-degree of freedom (DOF) motion of the main body 1 while the main body 1 is moved. The weight sensor 53 can be provided in the handle 12 of the main body 1 in order to detect whether the user's hand holding the handle 12 is applying a proper force.

The recording module 6 is provided in the control box 11 of the main body 1. The recording module 6 is signal-connected to and is controlled by the processing unit 2. The recording module 6 is provided with a wireless communication element 61 and serves to record the data processed and computed by the processing unit 2 (regarding the detection results of the inertia sensor 5) and to transmit the data wirelessly to a remote device, wherein the remote device can be a computer, server, or smartphone, for example. The recording module 6 is also provided with an alarm element which includes a loudspeaker 62 and a warning light 63. The loudspeaker 62 and the warning light 63 are provided on the control box 11 and are configured to send out a warning message if the inertia sensor 5 senses an abnormal condition while the user is walking with the quadruped walking stick. Abnormal conditions include the following: the quadruped base 13 of the main body 1 or the user's feet are not moved to the correct position, the user falls (i.e., the main body 1 topples or is tilted), the user is moving at abnormal speed, and the user's hand is not holding the handle 12 properly (i.e., not applying a proper force to the handle) 12).

The electricity module 7 is provided in the control box 11 of the main body 1. The electricity module 7 can be a lithium battery, dry battery, or solar cell and is separately electrically connected to the processing unit 2, the guiding module 3, the detection module 4, the inertia sensor 5, and the recording module 6 in order to provide the electricity required for their respective operations.

Figure 4:
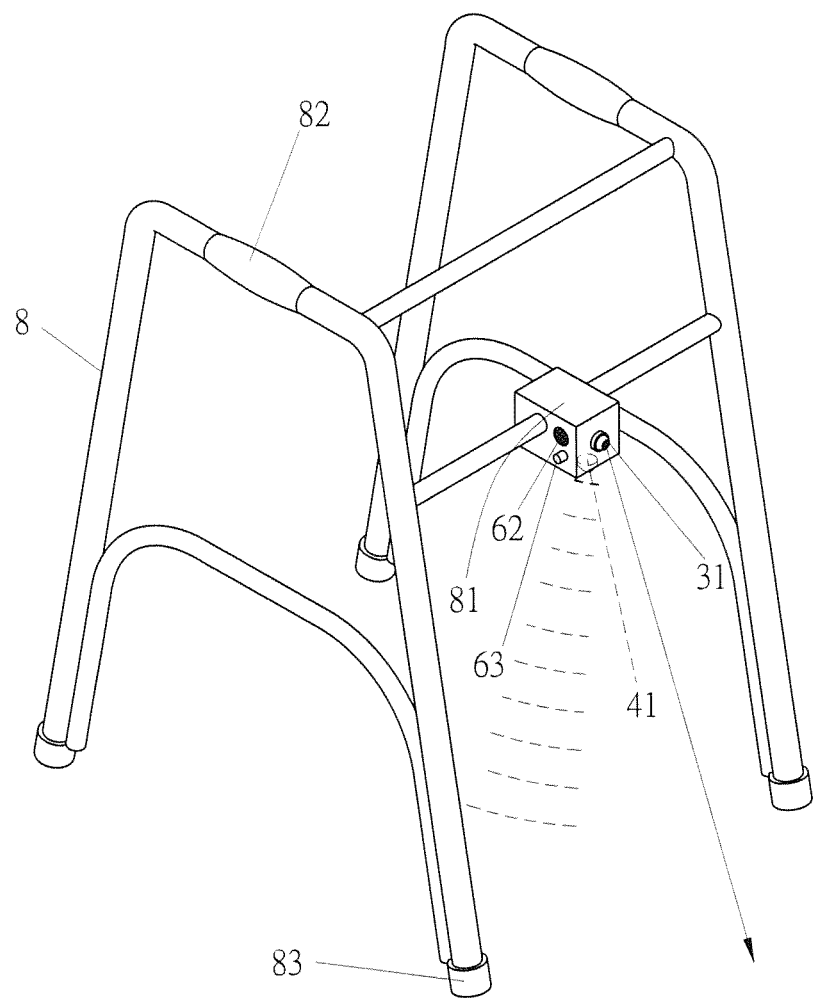
FIG. 4 is a perspective view of the walker in another embodiment of the present invention.

In another embodiment, the mobility aid with rehabilitative and guiding functions of the present invention is implemented as a walker. Referring to FIG. 4, the walker has a main body 8. The main body 8 is provided with a control box 81 at a proper position, a handle 82 at the top end, and a quadruped base 83 at the bottom end. The aforesaid processing unit 2, guiding module 3, detection module 4, inertia sensor 5, recording module 6, and electricity module 7 are provided in the control box 81 of the main body 8. The transmitter 31 of the guiding module 3 is provided at an exterior side of the control box 81 and can be driven to rotate through 360° as needed and to constantly project a visible light beam (e.g., laser beam) to the ground at a position in front of the main body 8. The detector 41 of the detection module 4 is also provided at an exterior side of the control box 81 and can be driven to rotate through 360° as needed and to constantly emit an ultrasonic wave to the ground at a position abreast of the main body 8, thereby defining an ultrasonic wave detection area abreast of the main body 8. The loudspeaker 62 and the warning light 63 of the recording module 6 are provided on the control box 81 and are configured to send out a warning message.

Figure 5:
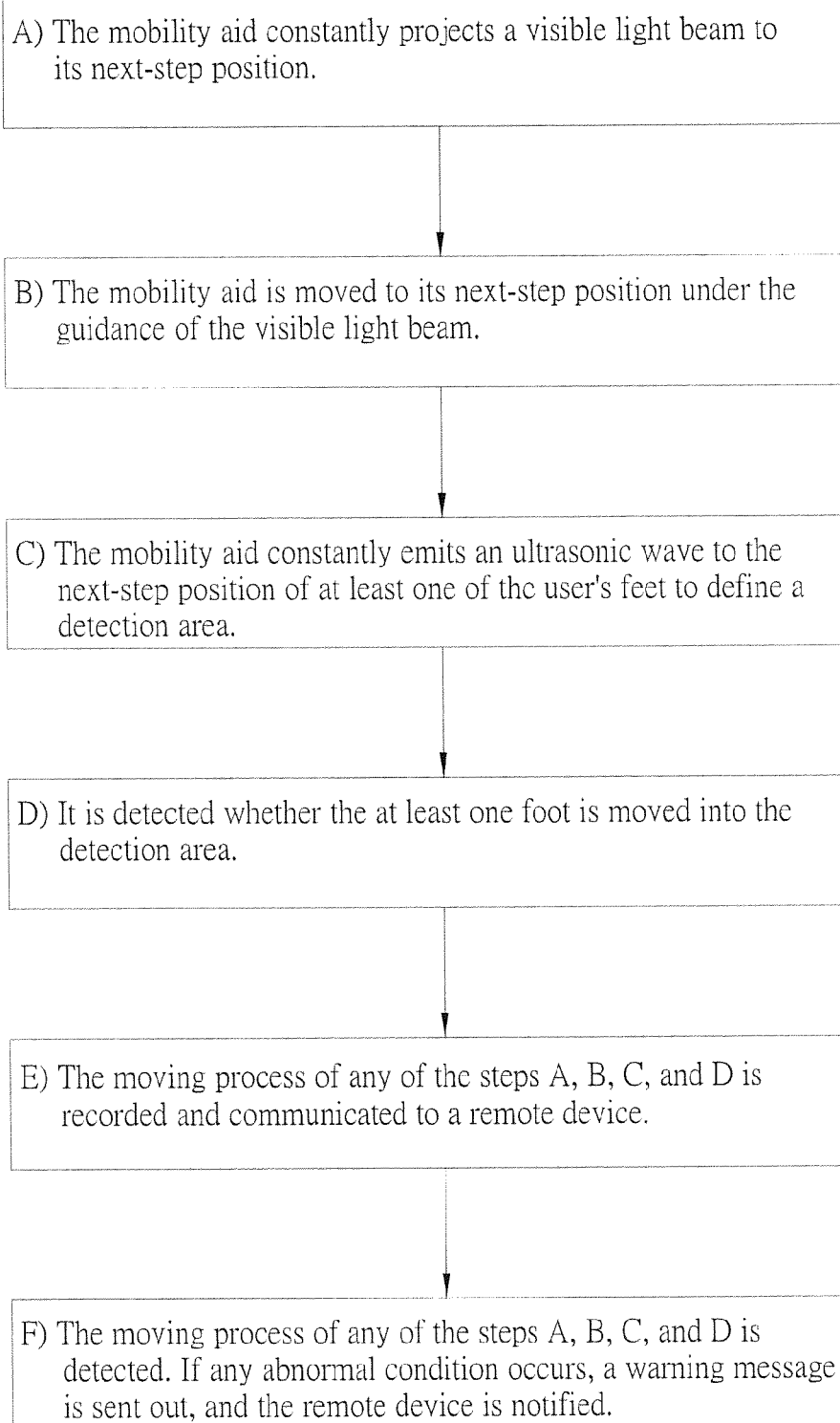
FIG. 5 is a flowchart of the rehabilitation and guiding method used by the mobility aid in one embodiment of the present invention.

The present invention also provides a rehabilitation and guiding method for use by a mobility aid such as the quadruped walking stick or walker described above. Referring to FIG. 5, the rehabilitation and guiding method for use by the foregoing quadruped walking stick includes the following steps.

Figure 6:
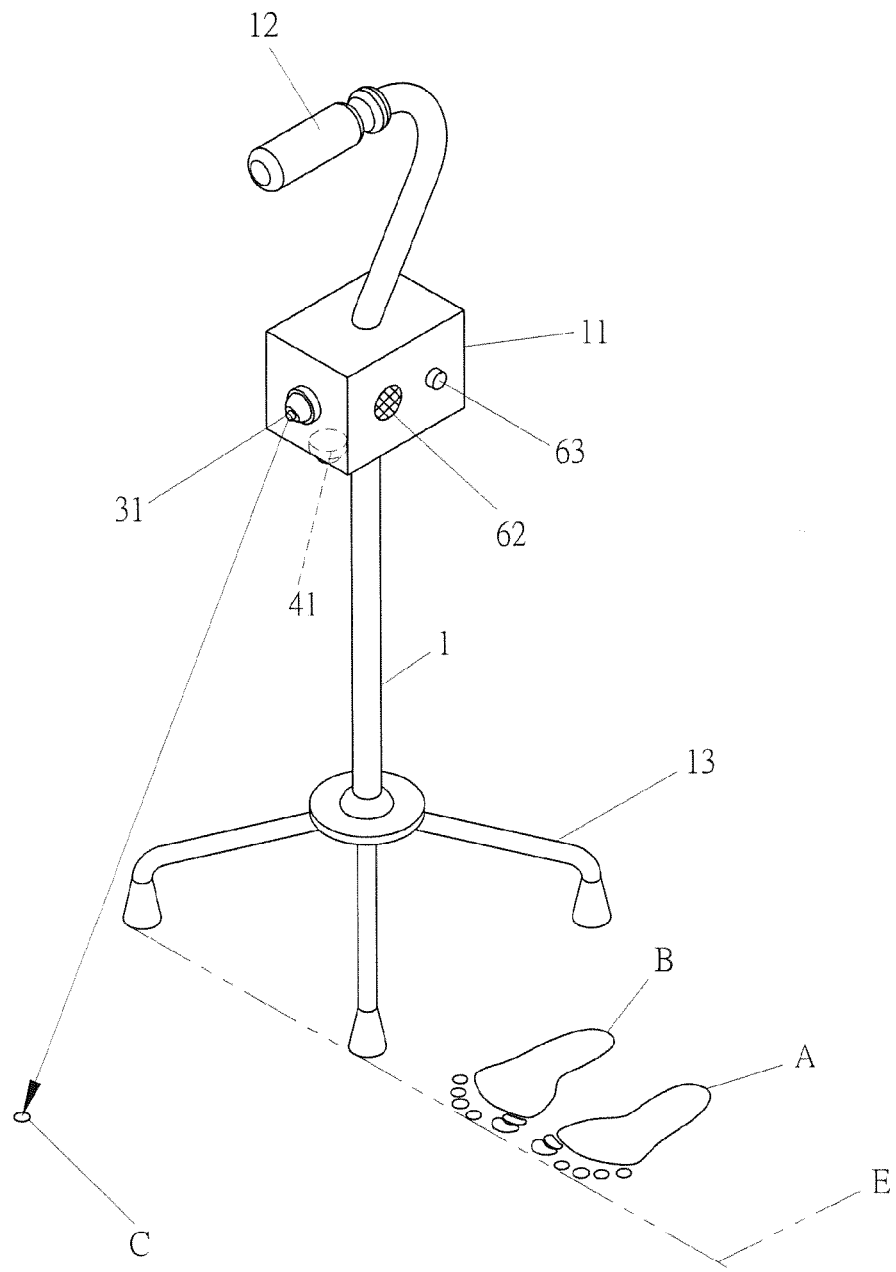
FIG. 6 schematically shows how the transmitter in one embodiment of the present invention constantly projects a visible light beam to the next-step position of the quadruped base.

A) The mobility aid keeps projecting a visible light beam to its next-step position. In this embodiment, it is assumed that the user's left foot A is injured and needs rehabilitation, and that the user's right foot B is healthy. To begin with, the mobility aid, the left foot A, and the right foot B are aligned along a baseline E, and the user has set the distance of one step (i.e., stride length) in a rehabilitative walk according to the rehabilitation condition of the injured foot and has input the stride length and the number of steps to be accomplished into the processing unit 2 in advance. Based on its computation result, the processing unit 2 drives the first power element 32 in the control box 11 into rotation so that the transmitter 31 is always rotated to a proper angle to constantly project a visible light beam (e.g., laser beam) to the ground at the next-step position C of the quadruped base 13 of the main body 1, wherein the next-step position C is in front of the baseline E, as shown in FIG. 6. The user at this moment has to hold the handle 12 of the main body 1 with his or her right hand, and the weight sensor 53 in the handle 12 will detect whether the user's hand is applying a proper force to the handle 12 when holding the handle 12.

Figure 7:
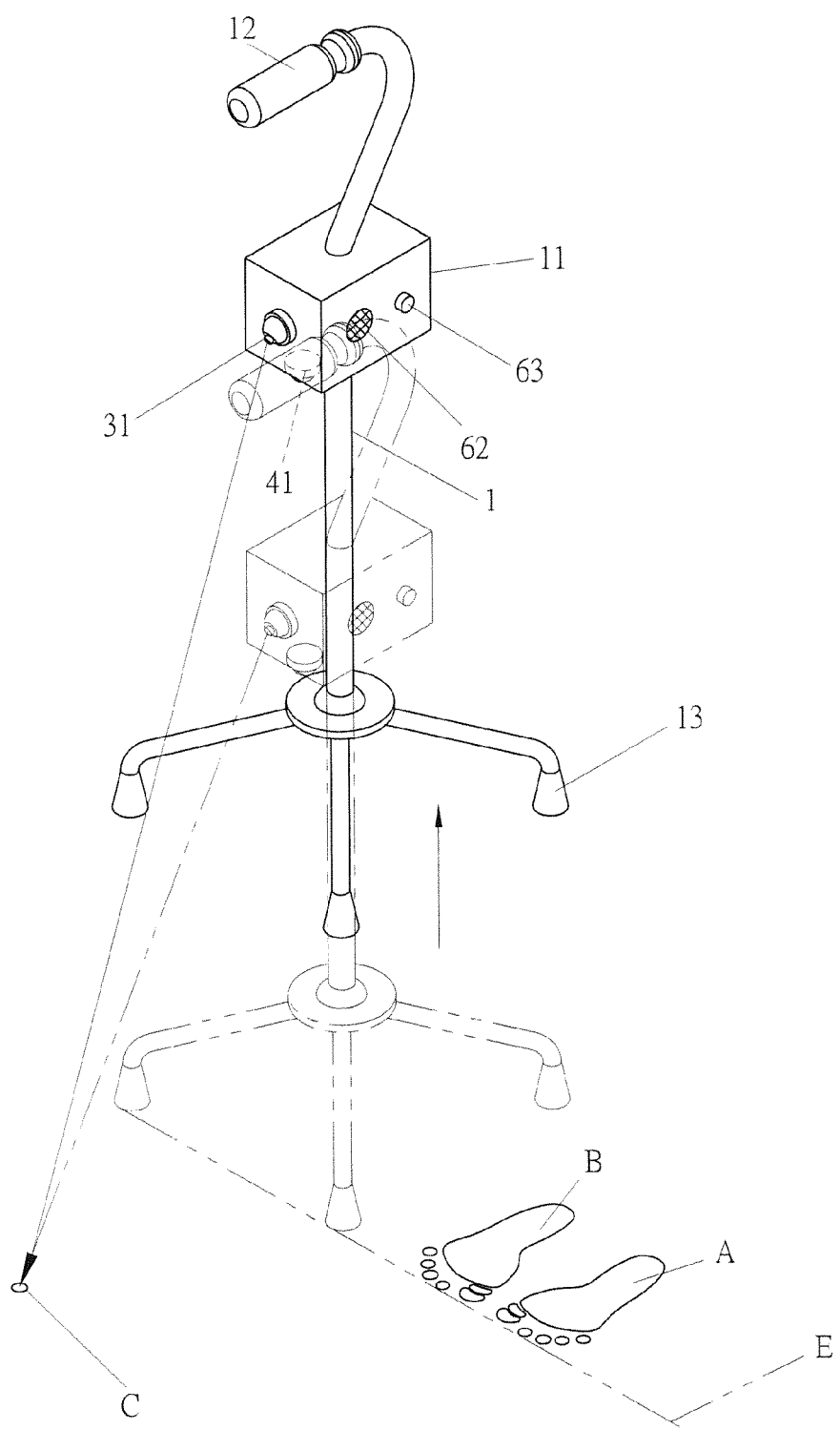
FIG. 7 schematically shows how the transmitter in one embodiment of the present invention rotates to constantly project the visible light beam to the next-step position of the quadruped base.
Figure 8:
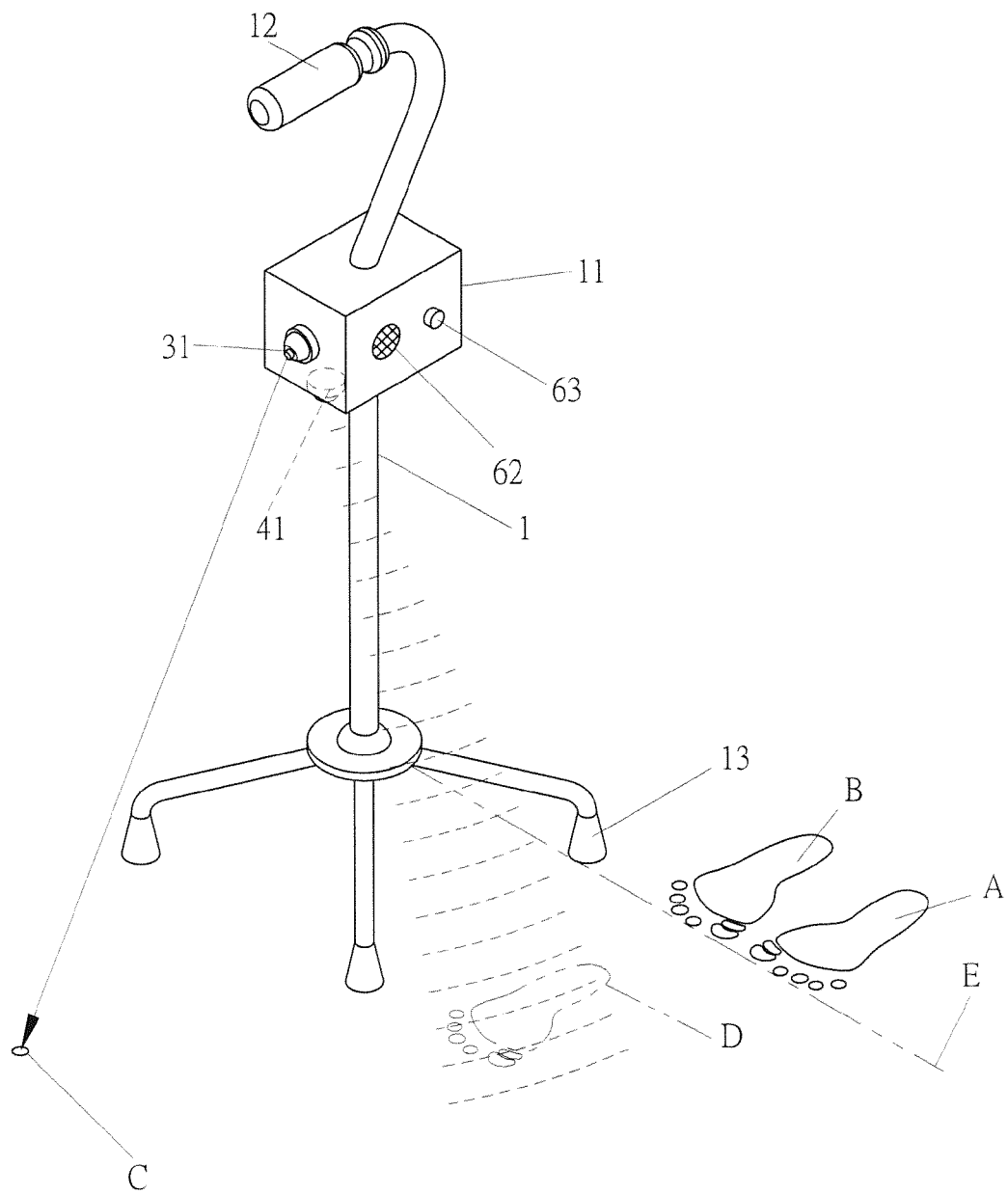
FIG. 8 is a schematic drawing in which the quadruped base in one embodiment of the present invention has been properly moved to and placed at the position indicated by the visible light beam.

B) The mobility aid is moved to its next-step position under the guidance of the visible light beam. That is to say, the user moves the quadruped base 13 of the main body 1 to the next-step position C in front of the baseline E according to the next-step position C indicated by the visible light beam. In the course in which the main body 1 is lifted, the inertia sensor 5 keeps detecting the change in position of the main body 1 and correcting the angle at which the transmitter 31 projects the visible light beam. More specifically, referring to FIG. 7, the first power element 32 in the control box 11 is rotated to keep the visible light beam of the transmitter 31 toward the next-step position C of the quadruped base 13, thereby guiding the user to move the quadruped base 13 of the main body 1 to the next-step position C, as shown in FIG. 8.

C) The mobility aid keeps emitting an ultrasonic wave to the next-step position of at least one of the user's feet to define a detection area. As shown in FIG. 8, the processing unit 2 drives the second power element 42 in the control box 11 into rotation according to the aforesaid computation result so that the detector 41 is always rotated to a proper angle to constantly emit an ultrasonic wave to the ground at the next-step position of the user's right foot B (i.e., the healthy foot) or left foot A (i.e., the injured foot) (or both feet in an alternate manner) in front of the baseline E, thereby defining a detection area D (shown also in FIG. 9), within which the detector 41 detects the landing position of a specific foot or either foot of the user. The ultrasonic wave detection area D is lateral to and abreast of the main body 1. In this embodiment, the detection area D is used to detect the user's right foot B (i.e., the healthy foot) by way of example.

Figure 9:
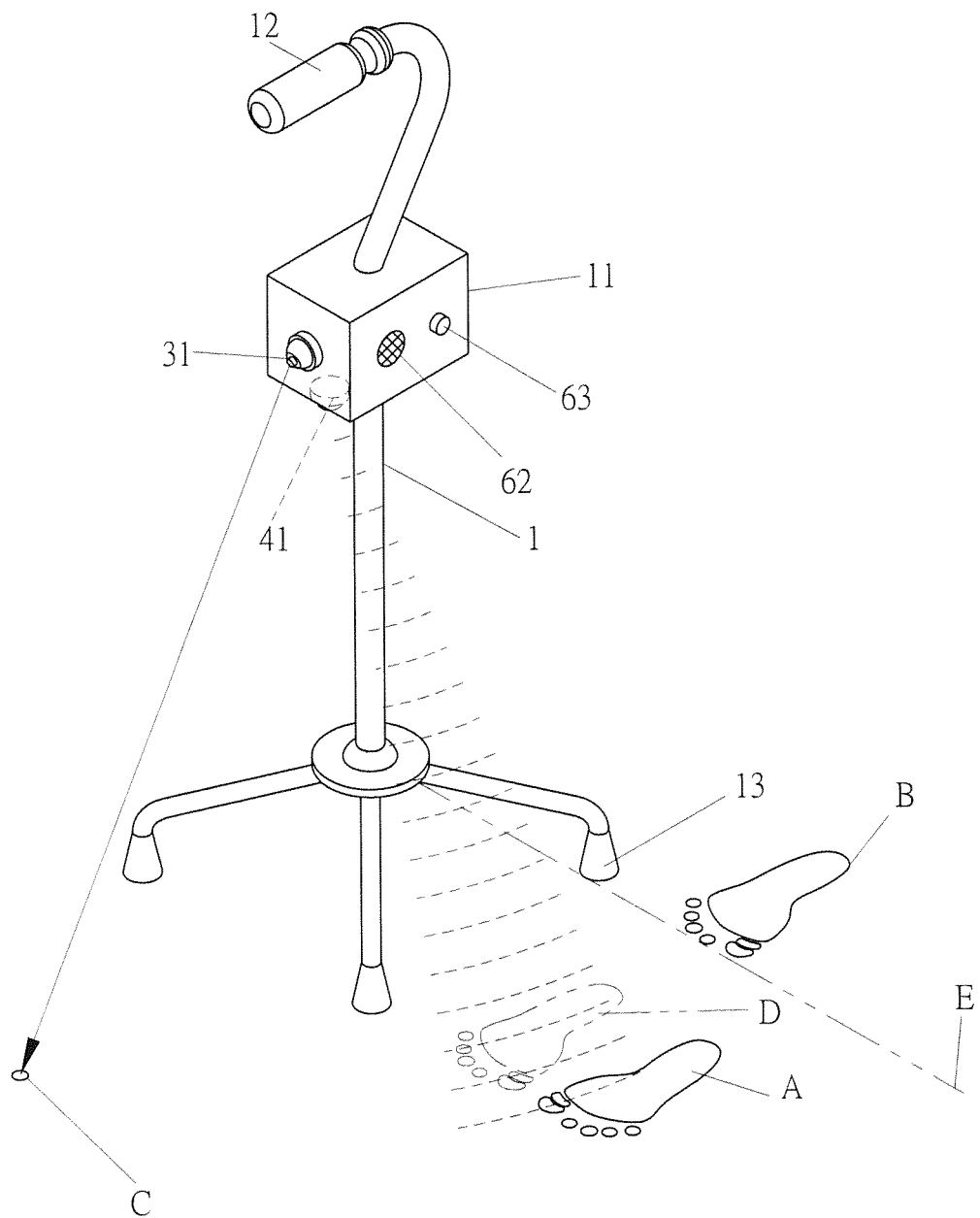
FIG. 9 schematically shows how the detector in one embodiment of the present invention constantly emits an ultrasonic wave to the next-step position of the user's right foot to define a detection area.
Figure 10:
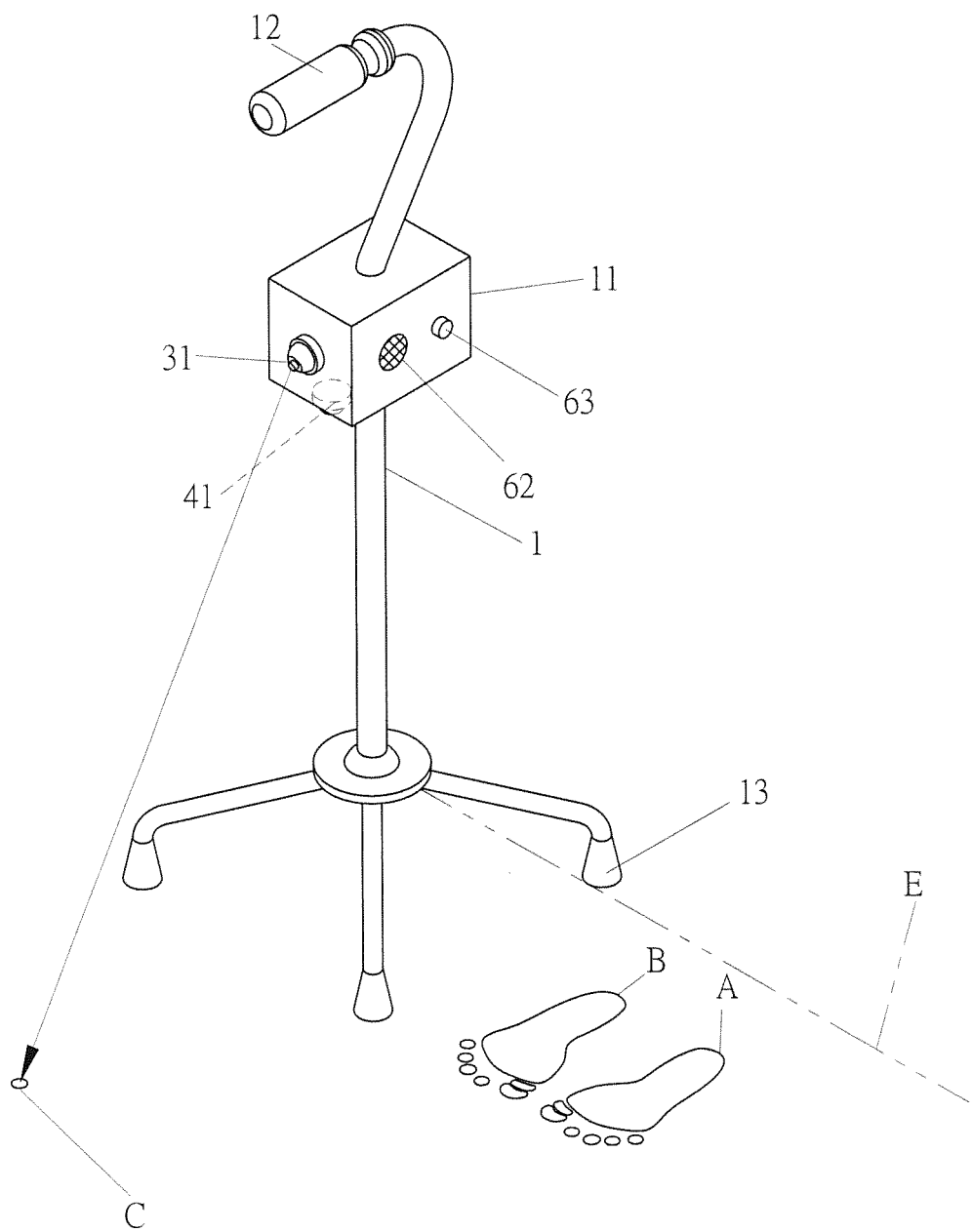
FIG. 10 is a schematic drawing in which the user's right foot has been properly moved to and placed in the detection area.

D) It is detected whether the at least one foot is moved into the detection area. As shown in FIG. 9, the user's left foot A (i.e., the injured foot) is moved to a position abreast of the quadruped base 13. Then, as shown in FIG. 10, the user's right foot B (i.e., the healthy foot) is moved into the ultrasonic wave detection area D. Thus, guided by the mobility aid, the user can keep on walking by sequentially moving the main body 1, the left foot A (i.e., the injured foot), and the right foot B (i.e., the healthy foot) over and over again, and in the meantime, the rehabilitation and guiding function of the present invention is achieved.

E) The moving process of any of the steps A, B, C, and D is recorded and communicated to a remote device. In the course in which either of the user's feet is moved and lands on the ground, the recording module 6 in the control box 11 of the main body 1 determines, according to the detection result of the detector 41, and records whether the foot lands at the correct position. The recording module 6 can also record such information as the acceleration, tilt, impact received, vibration, rotation, and multi-DOF motion of the main body 1 as detected by the inertia sensor 5 while the user is moving; and whether the user's hand is applying a proper force to the handle 12 when holding the handle 12. All such information is collected and computed by the processing unit 2 before being recorded by the recording module 6. In addition, the information is transmitted wirelessly through a wireless communication element 61 to a remote device such as a computer, server, or smartphone for validation of the rehabilitation result or as a reference for improvement.

F) The moving process of any of the steps A, B, C, and D is detected. If any abnormal condition is found, a warning message is sent out, and the remote device is notified. More specifically, in any of the user's aforesaid moving processes, the inertia sensor 5 detects whether the quadruped base 13 of the main body I is placed away from the next-step position C indicated by the visible light beam, whether the user falls (i.e., whether the main body 1 topples or is tilted), and whether the moving speed is abnormal. Meanwhile, the detector 41 detects whether the user's feet are moved to incorrect positions, and the weight sensor 53 in the handle 12 detects whether the user's hand holding the handle 12 is applying an improper force. Should any of the aforementioned abnormal conditions be detected, the information will be sent to and computed by the processing unit 2, recorded by the recording module 6, and transmitted wirelessly through the wireless communication element 61 to the remote device to call for rescue or demand improvement. The loudspeaker 62 and the warning light 63 will also produce a warning message (i.e., sound and light, respectively) to prompt the user for improvement or notify people nearby for help.

The mobility aid and the rehabilitation and guiding method described above are so designed that, while the user is moving, information related to each of the user's steps is continuously detected and recorded as a reference for rehabilitation and improvement.

The foregoing embodiments are but three of the contemplated embodiments of the present invention and should not be construed as restrictive of the scope of patent protection sought by the applicant. All simple equivalent changes and substitutions made according to the appended claims and the present specification should fall within the scope of the claims.

What is claimed is:

1. A mobility aid with rehabilitative and guiding functions, comprising:
   a main body having a control box, a handle, and a quadruped base, the control box being secured around a portion of the main body;
   a processing unit provided in the control box, said processing unit configured to store a pre-set stride length established for a user;
   a guiding module provided in the control box, the guiding module being signal-connected to the processing unit and to a rotatable transmitter, the transmitter being provided in the control box and controlled by a first power element, the first power element configured to drive the transmitter, the transmitter configured to rotate as needed through 360° and to constantly project a visible light beam to a ground at a next aid-placement position in front of the main body determined as a function of said pre-set stride length;
   a detection module provided in the control box, the detection module being signal-connected to the processing unit and to a rotatable detector, the detector being provided in the control box and controlled by a second power, the second power element configured to drive the detector, the detector configured to rotate as needed through 360° and to constantly emit an ultrasonic wave to the ground at a next foot-placement position abreast of the main body for detecting whether at least one of the user's feet is moved to the next foot-placement position and thereby whether a step movement of the user is consistent with the next aid-placement position generated by said guiding module;
   an inertia sensor provided in the control box, the inertia sensor being signal-connected to the processing unit, the inertia sensor including an accelerometer, an angular velocity sensor, and a weight sensor, the weight sensor being provided in the handle; and
   a recording module provided in the control box, the recording module being signal-connected to the processing unit, the recording module including a wireless communication element and an alarm element, the recording module configured to record data processed and computed by the processing unit and to transmit said data through the wireless communication element to a remote device, the alarm element configured to send out a warning message when said detection module has determined the user's step is inconsistent with the next step position generated by said guiding module or when another abnormal condition has been detected.

2. The mobility aid of claim 1, further comprising an electricity module provided in the control box, wherein the electricity module is separately electrically connected to and serves to provide electricity separately to the processing unit, the guiding module, the detection module, the inertia sensor, and the recording module.

3. The mobility aid of claim 1, wherein the first power element and the second power element each are a servomotor or stepper motor and are provided in the control box, and the alarm element includes a loudspeaker and a warning light.

4. The mobility aid of claim 1, wherein the mobility aid is a quadruped walking stick or a walker.

5. A rehabilitation and guiding method of a mobility aid, comprising:
   A) establishing a pre-set stride length for a user;
   B) storing said pre-set stride length into a processing unit;
   C) continuously projecting a visible light beam, by the mobility aid, to a next aid-placement position of the mobility aid, said next aid-placement position determined as a function of said pre-set stride length;
   D) moving the mobility aid to the next aid-placement position under guidance of the visible light beam;
   E) continuously emitting an ultrasonic wave, by the mobility aid, to a next foot-placement position of at least one of a user's feet to define a detection area;
   F) detecting whether the at least one of the user's feet is moved into the detection area by a rotatable detector capable of rotating through 360° ; and
   G) recording a moving process of any of the operations C, D, E and F and notifying a remote device of the moving process.

6. The rehabilitation and guiding method of claim 5, further comprising:

H) detecting the moving process of any of the operations C, D, E and F and, if at least one abnormal condition occurs, sending out a warning message and notifying the remote device.

7. The rehabilitation and guiding method of claim 6, wherein the at least one abnormal condition in the operation H is selected from from the group consisting of a quadruped base of the mobility aid not being placed at the next aid-placement position as indicated by the visible light beam, the mobility aid toppling or being tilted, the mobility aid being moved at an abnormal speed, and a handle of the mobility aid not being held with a proper force.

8. The rehabilitation and guiding method of claim 5, wherein the operation G includes:
  detecting, by an inertia sensor, information of the mobility aid while the mobility aid is being moved, the information including acceleration, tilt, impact received, vibration, rotation, and multi-degree of freedom (DOF) motion;
  recording the information by a recording module; and
  transmitting the information through a wireless communication element to the remote device, the remote device being selected from the group consisting of a computer, a server, and a smartphone.

9. The rehabilitation and guiding method of claim 5, wherein the operation C includes rotating a transmitter to a proper angle according to a computation result such that the transmitter constantly projects the visible light beam to the next aid-placement position, the next aid-placement position of the mobility aid being on a ground and in front of the mobility aid.

10. The rehabilitation and guiding method of claim 5, wherein:
  the operation A includes setting a stride length of a rehabilitative walk according to a rehabilitation condition;
  the operation B includes inputting the stride length and a required number of steps into said processing unit; and
  the operation E includes rotating a detector to a proper angle according to a computation result such that the detector constantly emits the ultrasonic wave to the next foot-placement position to define the detection area, the next foot-placement position being on a ground and in front of the at least one of the user's feet and abreast of the main body.

\* \* \* \* \*